United States Patent
Hu et al.

(10) Patent No.: US 9,469,639 B2
(45) Date of Patent: Oct. 18, 2016

(54) NAPHTHYLUREA DERIVATIVES AND MEDICAL APPLICATIONS THEREOF

(71) Applicant: RADIANT PHARMA & TECH. CO., LTD., Zhenjiang, Jiangsu (CN)

(72) Inventors: Yingjian Hu, Zhenjiang (CN); Zhibin Luo, Zhenjiang (CN); Yanhong Zhang, Zhenjiang (CN); Li Han, Zhenjiang (CN); Yun Wang, Zhenjiang (CN); Hongfei Lu, Zhenjiang (CN)

(73) Assignee: Radiant Pharma & Tech. Co., Ltd., Zhenjiang, Jiangsu Province (CN)

( * ) Notice: Subject to any disclaimer, the term of this patent is extended or adjusted under 35 U.S.C. 154(b) by 0 days.

(21) Appl. No.: 15/024,300

(22) PCT Filed: Aug. 20, 2014

(86) PCT No.: PCT/CN2014/084816
§ 371 (c)(1),
(2) Date: Mar. 24, 2016

(87) PCT Pub. No.: WO2015/043342
PCT Pub. Date: Apr. 2, 2015

(65) Prior Publication Data
US 2016/0207916 A1    Jul. 21, 2016

(30) Foreign Application Priority Data
Sep. 29, 2013  (CN) .......................... 2013 1 0455924

(51) Int. Cl.
*C07D 471/04* (2006.01)
*C07D 231/56* (2006.01)

(52) U.S. Cl.
CPC ........... *C07D 471/04* (2013.01); *C07D 231/56* (2013.01)

(58) Field of Classification Search
None
See application file for complete search history.

(56) References Cited

FOREIGN PATENT DOCUMENTS

| | | |
|---|---|---|
| CN | 101146534 A | 3/2008 |
| CN | 103214479 A | 7/2013 |
| WO | 2006/050109 A2 | 5/2006 |
| WO | 2006/050109 A3 | 5/2006 |
| WO | 2007/144202 A1 | 12/2007 |
| WO | 2011/046991 A3 | 4/2011 |

*Primary Examiner* — Brian J Davis
(74) *Attorney, Agent, or Firm* — Connie Ding; Peter L. Brewer; Baker Donelson IP Group

(57) ABSTRACT

The present invention relates to naphthylurea derivatives. Such substances can significantly inhibit VEGFR2 and PDGFR-β receptor tyrosine kinase phosphorylation at nanomolar concentration levels. It is a novel type of tyrosine kinase inhibitors which can be used in the treatment of tyrosine kinase-mediated diseases or symptoms such as malignancies and ocular diseases accompanied with pathologic neovascularization.

14 Claims, No Drawings

NAPHTHYLUREA DERIVATIVES AND MEDICAL APPLICATIONS THEREOF

CROSS REFERENCE TO RELATED APPLICATIONS

This application is a §371 National State Application of PCT/CN2014/084816 filed Aug. 20, 2014, which claims priority to CN 201310455924.6 filed Mar. 29, 2013, which are hereby incorporated by reference in their entirety.

TECHNICAL FIELD

The invention belongs to bio-medical field, particularly to a novel kind of naphthylurea derivatives and medical applications thereof.

BACKGROUND OF THE INVENTION

Age-related macular degeneration (AMD) is the leading cause of blindness in elderly people over the age of 50. Diabetic retinopathy (DR) is the most common cause of blindness in young and middle-aged people. Clinical or animal models demonstrated that VEGF/KDR or PDGF/PDGFR-β was abnormally high in the diseased tissues. The severity of choroidal or retinal pathological neovascularization was significantly positively correlated with the level of VEGF/KDR expression in the diseased tissues. Anti-VEGF antibodies or tyrosine kinase inhibitors can effectively inhibit the formation of neovascularization. Inhibiting the phosphorylation of KDR and PDGFR receptor tyrosine kinase as a target for drug development has become the newest strategy for the treatment of ocular neovascularization. VEGFR receptors are mainly expressed in vascular endothelial cells and tumor cells. Vascular endothelial growth factor receptor-2 (KDR) plays a key role in the formation of neovascularization. VEGFR receptors mainly expressed in endothelial cells and tumor cells. Novel naphthylurea derivatives ascular endothelial growth factor receptor-2 (KDR) plays a key role in the formation of new blood vessels. PDGFR receptors mainly express in vascular wall cells. PDGFR-β receptor plays a major role in maintaining the integrity of the blood vessel wall. VEGF or PDGF growth factor produces biological effects by the phosphorylation of receptor kinase thereof. Lucentis fails to meet clinical needs. 60% of wet AMD patients still fail to respond to Lucentis therapy, and need intraocular injection once a month resulting in potentially serious ocular complications. The efficacy of anti-VEGF-only therapy is limited. The price of Lucentis is very expensive, and a patient needs 12 injections every year and pays an annual payment of 28000 US dollars (about 180000 China Yuan). Therefore, developing a reliable, easily administrating and cheaper drug has become one of the objectives of the major pharmaceutical companies in the world. It is also one of the medical application blanks desired to be filled.

Clinical and scientific researches have fully proved that abnormal KDR expression and intracellular signal transduction play an important role in formations of pathological choroidal or retinal neovascularization. After KDR binding with its specific ligand VEGF, receptor tyrosine kinase is autophosphorylated and induces a series of intracellular signal transduction, resulting in the proliferation and migration of vascular endothelial cells and angiogenesis. Therefore, inhibiting the phosphorylation of KDR receptor tyrosine kinase can effectively block the abnormal intracellular signal transduction induced by KDR, and reduce pathological choroidal or retinal neovascularization, and thereby prevents the severe visual loss caused by choroidal or retinal bleeding, scarring and fibrosis induced by neovascularization. For example, Drug Lucentis or Macugen (both are VEGF antibodies) approved by the United States FDA presently is used for the treatment of age-related macular degeneration. Moreover, clinical data has demonstrated that intraocular injection of Lucentis or Macugen can effectively prevent the eyesight of patients with age-related macular degeneration from further fading by inhibiting the VEGF/KDR expression-induced abnormal intracellular signal transduction. In addition, PDGFR also involves in the formation of neovascularization and inhibits phosphorylation of PDGFR receptor tyrosine kinase, which can cause the auto-apoptosis of perithelial cells of the pathological choroidal or retinal neovascularization reluting in degenerative changes and atrophies of the pathological new vessels such that vision is effectively improved. Therefore, drug designs targeting to control VEGF/KDR and/or PDGF/PDGFR abnormal expression and signal transduction have become new strategies of treating age-related macular degeneration and diabetic retinopathy.

In addition, the occurrence, development and metastasis of many tumors and the formation of tumor neovascularization are closely related with the abnormal expression of tyrosine kinase. Particularly, some tyrosine kinase receptors abnormally express in solid tumor cells, wherein vascular endothelial cell growth factor receptor (VEGFR) highly expresses both in many tumor cells and tumor vascular endothelial cells, and platelet-derived growth factor receptor (PDGFR) abnormally expresses in tumor stromal fibroblasts. The autocrine loop formed by ligands and receptors of tyrosine kinase directly participates in the occurrence and development of tumor cells, for example, vascular endothelial cell growth factor receptor (VEGFR) exist in melanoma; platelet-derived growth factor receptor (PDGFR) exist in glioma; and stem cell growth factor receptor (KIT) exist in small cell lung cancer, and the like. In addition, similar loops exist in melanoma, meningioma, neuroendocrine tumors, ovarian cancers, prostate cancers, lung cancers and pancreatic cancers. These loops closely link with the occurrence and development of tumors. Stem cell growth factor (Kit) is ligand of stem cell growth factor receptors (SCFR, c-KIT). KIT/SCFR have a very close relationship with hematopoietic function of body, and development of mast cells and Cajal interstitial cells. The study found that there are more than 30 function-acquired mutation versions of KIT/SCFR, which are the direct inducements of occurrence and development of many tumors. Furthermore, the autocrine loop of KIT/SCFR exists in 70% of patients with small cell lung cancer, and helps the cancers to develop independent of growth factors. In addition, the occurrence, development and metastasis of solid tumors are dependent on formation of tumor neovascularization which provides essential nutrients and oxygen for the growth of tumor. Tumor angiogenesis is an important process for invasion, migration and proliferation of cancer cells. Vascular endothelial cell growth factor receptor (VEGFR) family and platelet-derived growth factor receptor (PDGFR) family are directly related with occurrence and development of tumor and formation of tumor angiogenesis. Vascular endothelial growth factor (VEGF), known as the most powerful vascular penetrant and endothelial cell-specific mitogen, plays an important role in proliferation, migration and angiogenesis of endothelial cells. The expression level of VEGF shows an obviously positive correlation with the vascularization degree of tumor tissue. VEGF mainly acts on high affinity receptors VEGFR-1 and KDR in endothelial cells which have different signal transduction pathways such that tyrosine kinase is phosphorylated to play its biological action. KDR plays a key role in growth, metastasis and angiogenesis of tumor. Platelet-derived growth factor (PDGF) and its receptor (PDGFR) involve with pathogenesis of multiple tumors, and play important roles in angiogenesis. Platelet-derived growth factor (PDGF) shows its cell biological effects via its receptor (PDGFR). PDGFR maintains the integrity of the vascular wall and promotes the formation of tumor neovascularization by regulating the proliferation and migration of vascular wall perithelial cells and vascular smooth muscle cells. Moreover, the growth of tumor is promoted by changing the microenvironment within tumor.

Due to the abnormal expression of tyrosine kinase is closely related with the occurrence, development, metastasis and neovascularization of tumor, drug research and development targeting tyrosine kinase has become a focus of anti-tumor drugs research in the world. Especially, it is a new strategy to treat cancer that targeting neovascularization to inhibit the formation of tumor angiogenesis and block nutrient supply and migration path of tumor to prevent growth and metastasis of tumor. The abnormal expression of KDR or PDGFR receptors plays a key role in the formation of tumor neovascularization, and therefore KDR or PDGFR receptors have become the most ideal target of anti-tumor drug therapy. Furthermore, two anti-tumor drugs Sorafenib and Sunitinib (SU11248) mainly inhibiting KDR and PDGFR receptor tyrosine kinase, approved by the US Food and Drug Administration (FDA), have fully proved their anti-tumor therapeutic effects with high curative effects and fewer side effects in clinical practice.

SUMMARY

The present invention is intended to provide naphthylurea derivatives, which can be used as tyrosine kinase inhibitors, and which can significantly inhibit phosphorylation of VEGFR2 and PDGFR-β receptor tyrosine kinase at nanomolar concentration level.

This invention also provides the applications of the naphthylurea derivatives in preparation of medicines treating tyrosine kinase-mediated diseases or symptoms.

To solve the above problems, the present invention on one hand provides a naphthalurea derivative being compound of formula I, and a pharmaceutically acceptable salt, a hydrate, a pro-drug or a metabolite produced in any type of metabolism thereof,

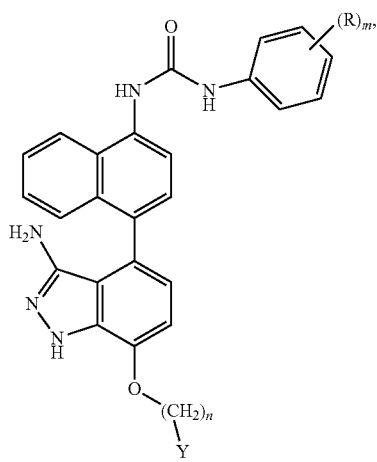

in formula I,
R is selected from the group consisting of: halogen; hydroxyl; sulfhydryl; cyano; amino or alkyl-substituted amino; nitryl; $C_1 \sim C_6$ alkyl unsubstituted or substituted by one or more of halogen, hydroxyl, sulfhydryl, cyano, amino, alkyl-substituted amino and nitryl; $C_1 \sim C_6$ alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; $OCOR_9$;

M is an integer between 0 and 5;
N is an integer between 1 and 5;
Y is selected from the group consisting of: halogen; hydroxyl; amino or alkyl-substituted amino; $C_1 \sim C_3$ alkoxy unsubstituted or substituted by one or more of halogen, hydroxyl, sulfhydryl, cyano, amino and alkyl-substituted amino; five-membered or six-membered heterocycle containing N and/or O; $CHR_{10}R_{11}NH_2$. $R_5$, $R_6$, $R_7$, $R_8$, $R_9$, $R_{10}$, and $R_{11}$ are independently selected from $C_1 \sim C_6$ alkyl unsubstituted or substituted by halogen.

According to a further implementation of this invention, in formula I, R is preferably selected from the group consisting of: fluoro, chloro, bromo, iodo, hydroxyl, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, $C(=O)CH_3$, $C(=O)CH_2CH_3$, $C(=O)NHCH_3$, $C(=O)NHCH_2CH_3$, $NHC(=O)OCH_3$, $NHC(=O)OCH_2CH_3$, $NHCH_3$, $N(CH_3)_2$, and $NHCH_2CH_3$.

According to an embodiment of the present invention, in formula I, in particular, m can be 0, 1, 2, 3, 4 or 5. Preferably, m is 1 or 2. In formula I, in particular, n can be 1, 2, 3, 4 or 5. Preferably, n is 2 or 3.

Preferably, Y is selected from the group consisting of:

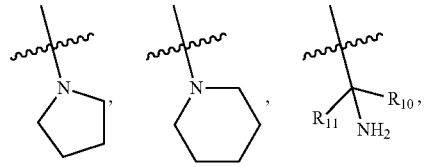

wherein, $R_{10}$ and $R_{11}$ are independently selected from the group consisting of: methyl, halogen-substituted methyl, halogen-substituted ethyl, propyl or halogen substituted propyl.

According to a specific and preferable aspect, Y is $CH(CH_3)_2NH_2$.

The typical compound of formula I can be listed as follow:

(V)

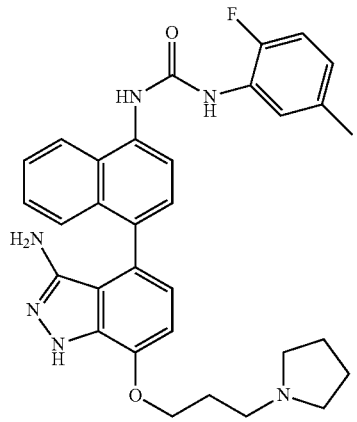

-continued

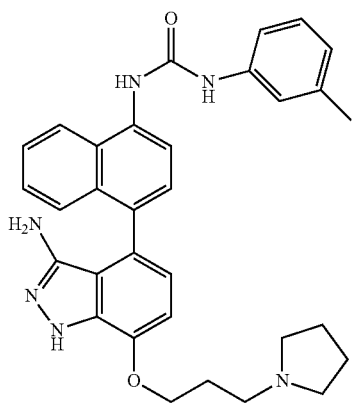

(VI)

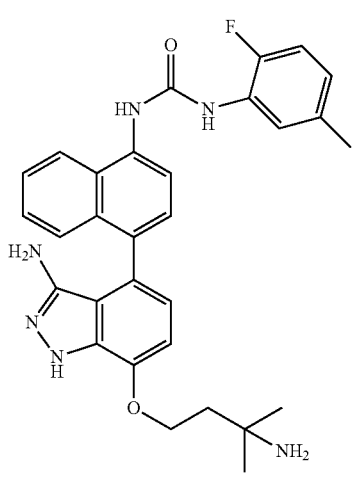

(VII)

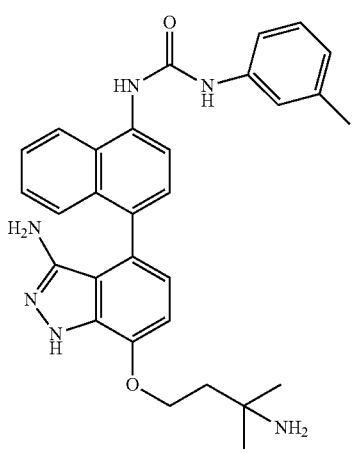

(VIII)

Another aspect of the present invention provides another naphthalurea derivative, compound of formula II, and a pharmaceutically acceptable salt, a hydrate, a pro-drug or any metabolite produced in any type of metabolism thereof;

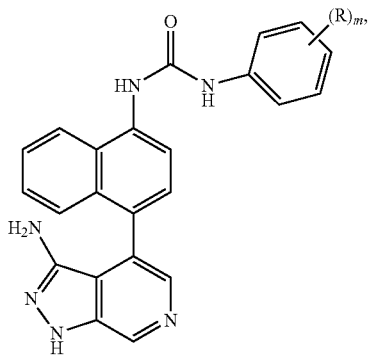

(II)

in formula II,

R is selected from the group consisting of: halogen; hydroxyl; sulfhydryl; cyano; amino or alkyl-substituted amino; nitryl; C1~C6 alkyl unsubstituted or substituted by one or more of halogen, hydroxyl, sulfhydryl, cyano, amino, alkyl-substituted amino and nitryl; C1~C6 alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; $OCOR_9$, wherein $R_5$, $R_6$, $R_7$, $R_8$ and $R_9$ are independently selected from $C_1$~$C_6$ alkyl unsubstituted or substituted by halogen;

M is an integer between 0 and 5;

According to a specific embodiment of the present invention, in formula II, m can be 0, 1, 2, 3, 4 or 5. Preferably, m is 1 or 2, and R is selected from $C_1$~$C_6$ alkyl and halogen. More preferably, when m is 1, R is selected from $C_1$~$C_6$ alkyl; when m is 2, R is selected from $C_1$~$C_6$ alkyl and halogen.

The typical compounds of formula II are listed as follow:

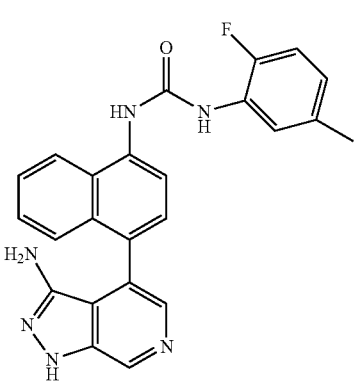

(III)

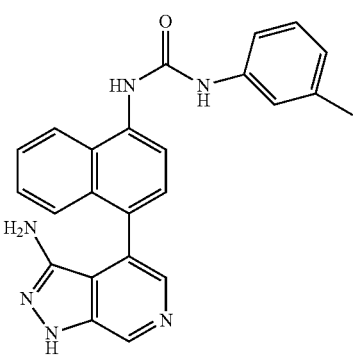

(IV)

According to an embodiment of the present invention, the compound includes not only a single compound, but also includes a mixture of various compounds whose structure satisfies the requirements of the formula, as well as different isomers of the same compound such as racemates, enantiomers, diastereomers, and the like. The pharmaceutically acceptable salt includes, but is not limits to, hydrochloride, hydrobromide, phosphate, sulfate, acetate, trifluoroacetate, maleate, methanesulfonate, benzenesulfonate, benzoate, methyl besylate, succinate, fumarate, tartrate, gallate, citrate, and the like. The "pro-drug of compound of formula I or II" refers to a substance which can be converted into at least one compound of formula I or II or salts thereof by metabolic or chemical reactions in volunteers when administered by using appropriate methods.

The invention also provides use of the above naphthalurea derivatives in preparation of drugs treating tyrosine kinase-mediated diseases or symptoms.

The tyrosine kinase-mediated diseases or symptoms include malignancies and ocular diseases accompanied with pathological neovascularization.

Still another aspect of the present invention provides medicine for treating diseases mediated by tyrosine kinase, the effective constituents of which contains the above-mentioned naphthalurea derivatives of this invention at least.

According to a specific embodiment of the present invention, diseases or symptoms mediated by tyrosine kinase include malignancies and ocular diseases accompanied with pathological neovascularization. Malignancies include, but are not limited to, kidney cancer, liver cancer, colon cancer, gastrointestinal stromal tumors, lung cancer, breast cancer, pancreatic cancer, neural glial tumor, lymph cancer, fivrosarcoma, ovarian cancer, leukemia and prostate cancer, etc. Ocular diseases include age-related macular degeneration, diabetic retinopathy and neovascular glaucoma and other eye diseases.

The compound according to the present invention can be obtained by using conventional synthetic methods in the art of organic synthesis.

Due to the use of the above mentioned technical schemes, the present invention has the following advantages over the prior art:

The invention provides novel tyrosine kinase inhibitors having tyrosine kinase inhibition activity, naphthyl structure of which increases the lipotropy of central section of molecule and thus the binding interaction between molecule and receptor increases. Hydrogen bonding between Naphthalurea structure which can bring hydrogen-bond interaction carried by the compound further increases the binding interaction between the molecule and receptors. Due to the strong inhibition activity of tyrosine kinase, the compound can be used for treating of malignancies and eye diseases such as age-related macular degeneration diseases, diabetic retinopathy and neovascular glaucoma. In addition, the naphthalurea derivatives of the present invention, particularly the naphthalurea derivatives with formula I, have high solubility in water.

DETAILED DESCRIPTION

In the following, the present invention is explained in detail combing with the specific embodiments, however, the present invention is not limited to those embodiments.

Preparation of Naphthalurea Derivatives of Formula I and II

Taking compounds (III), (IV), (V), (VI), (VII) and (VIII) for example, the preparation of naphthalurea derivatives is described.

By retrosynthetic analysis of the target compounds, compounds (III), (IV) and (V) could be split into four segments, segments A, B, C and D, which are synthesized respectively.

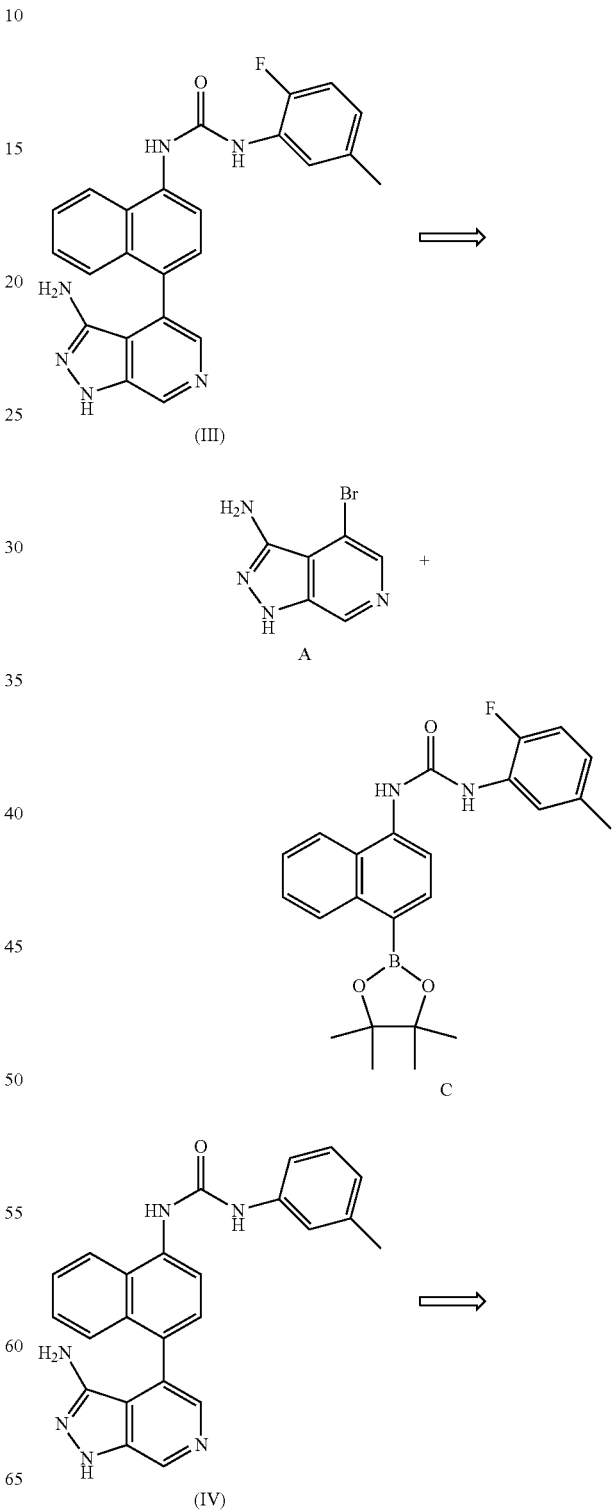

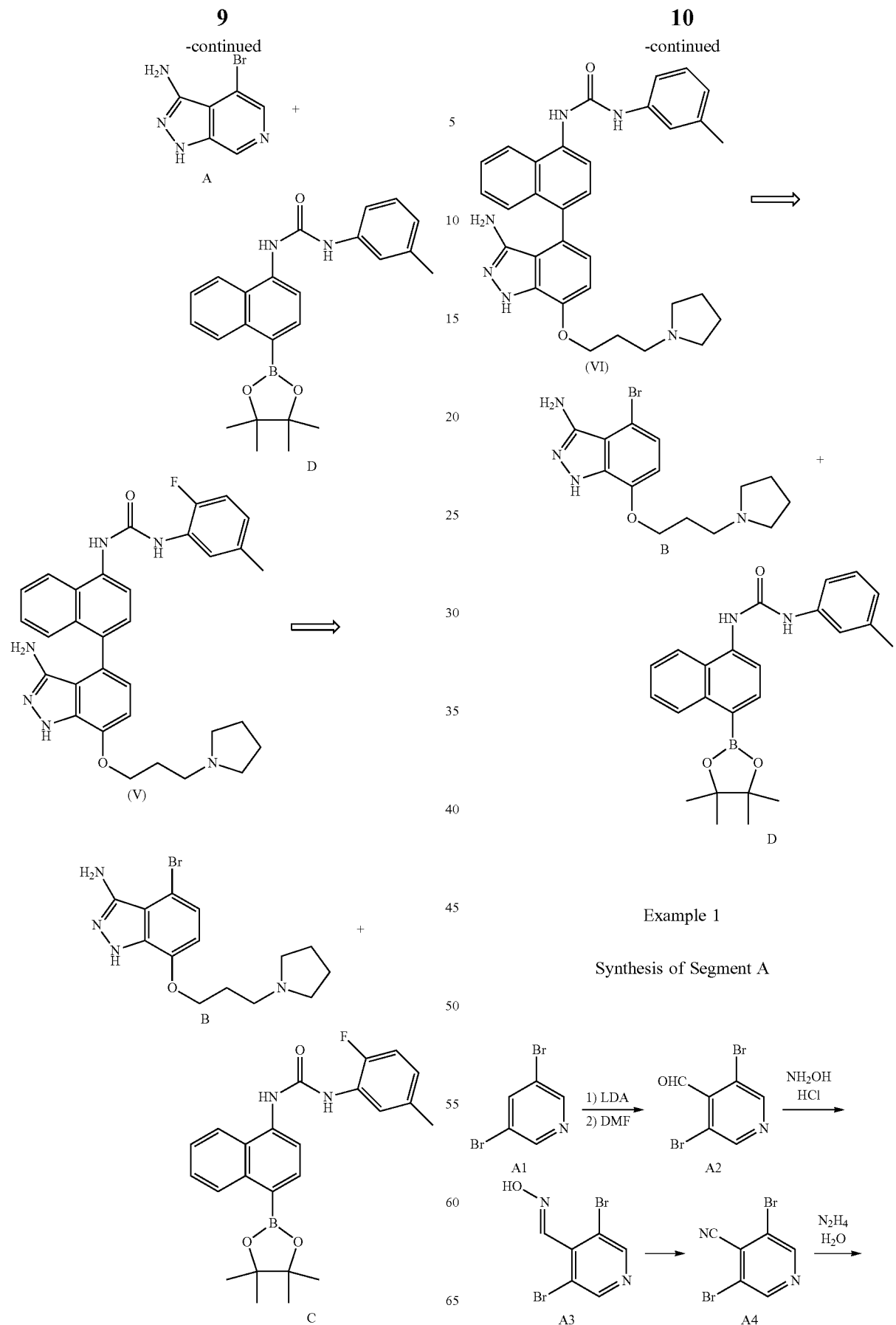
Example 1
Synthesis of Segment A

-continued

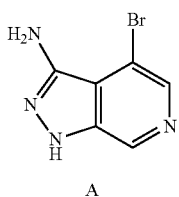
A

1.1 Synthesis of Compound A2

Under nitrogen protection, 150 mL anhydrous THF and 49.1 g diisopropylamine were added into a 2 L three-necked flask, and the solution was cooled to −5° C. 194 mL 2.5M n-BuLi solution was dropwise added in, and meanwhile the temperature was kept at or below 0° C., and after dropwise adding finished, the system was kept at the temperature and reacted for 1 hour, and then the solution was cooled to −70° C. 100 g 3,5-dibromopyridine dissolved in 500 mL THF was dropwise added with keeping temperature ≤−70° C., and after the dropwise adding finished, the system was kept at the temperature and stirred for 2 hours. 61.6 g DMF dissolved in 250 mL THF was dropwise added into the resulted system with keeping temperature ≤−70° C., and stirred for 2 hours. The reaction had completed by checking by TLC. The reaction liquid was added into 2.5 L saturated sodium bicarbonate solution, extracted by ethyl acetate (800 mL×3). The organic phases were merged, washed by saturated salt water, dried by anhydrous sodiumsulfate, concentrated and recrystallized with petroleum ether to give a yellow solid, i.e. compound A2, 50 g, 45% yield. $^1$H-NMR (400 MHz, DMDO-d6) (ppm) 8.91 (s, 2H), 10.09 (s, 1H).

1.2 Synthesis of Compound A3

62 g compound A2, 17.1 g hydroxylamine hydrochloride, 15.6 g sodium carbonate, 400 mL methanol and 200 mL water were respectively added into a 1 L three-necked flask, and reacted at room temperature for 2 hours. The reaction had substantially completed by checking by TLC. The reaction liquid was filtered, and the filtered cake was added into a single necked flask, stirred to dissolve to be clarified after adding in 1 L ethyl acetate and then stratified to remove the lower aqueous layer. The organic layer was dried by anhydrous sodium sulfate, filtered, and concentrated to dryness. 200 mL petroleum ether was added, and the resulted system was stirred well, filtered and dried to give a white solid, i.e. compounds A3, 55 g, 84% yield. $^1$H-NMR (400 MHz, DMDO-d6) (ppm) 8.16 (s, 1H), 8.81 (s, 2H), 12.21 (s, 1H).

1.3 Synthesis of Compound A4

55 g compound A3 was added into a 1 L of three-necked flask and dissolved in 550 mL DMF. The solution was placed in ice-water bath, and 35 g triphosgene was portionwise added in and then reacted for 30 minutes. The reaction had substantially completed by checking by TLC, and 1 L water was added to quench the reaction. The system was extracted with dichloromethane (500 mL×3). The organic phases were merged, washed by saturated salt water for two times, dried by anhydrous Na$_2$SO$_4$, concentrated, mashed with petroleum ether, and filtered to give a flesh-colored solid, i.e. compounds A4, 46 g, 90% yield. $^1$H-NMR (400 MHz, CDCl3) (ppm) 8.84 (s, 2H).

1.4 Synthesis of Segment A 45 g compound A4, 51.1 g 85% hydrazine hydrate and 125 mL n-butanol were added into a 500 mL single-necked flask, heated and refluxed for 24 hours. The reaction had substantially completed by checking by TLC. The reaction liquid was concentrated to nearly dry and filtered. The filter cake was mashed with 200 mL water and filtered. The filter cake was mashed with 100 mL methanol, filtered, and dried to give an off-white solid, i.e. segment A, 26 g, 71% yield. $^1$H-NMR (400 MHz, DMDO-d6) (ppm) 5.35 (s, 2H), 8.10 (s, 1H), 8.72 (s, 1H), 12.43 (s, 1H).

Example 2

Synthesis of Segment B

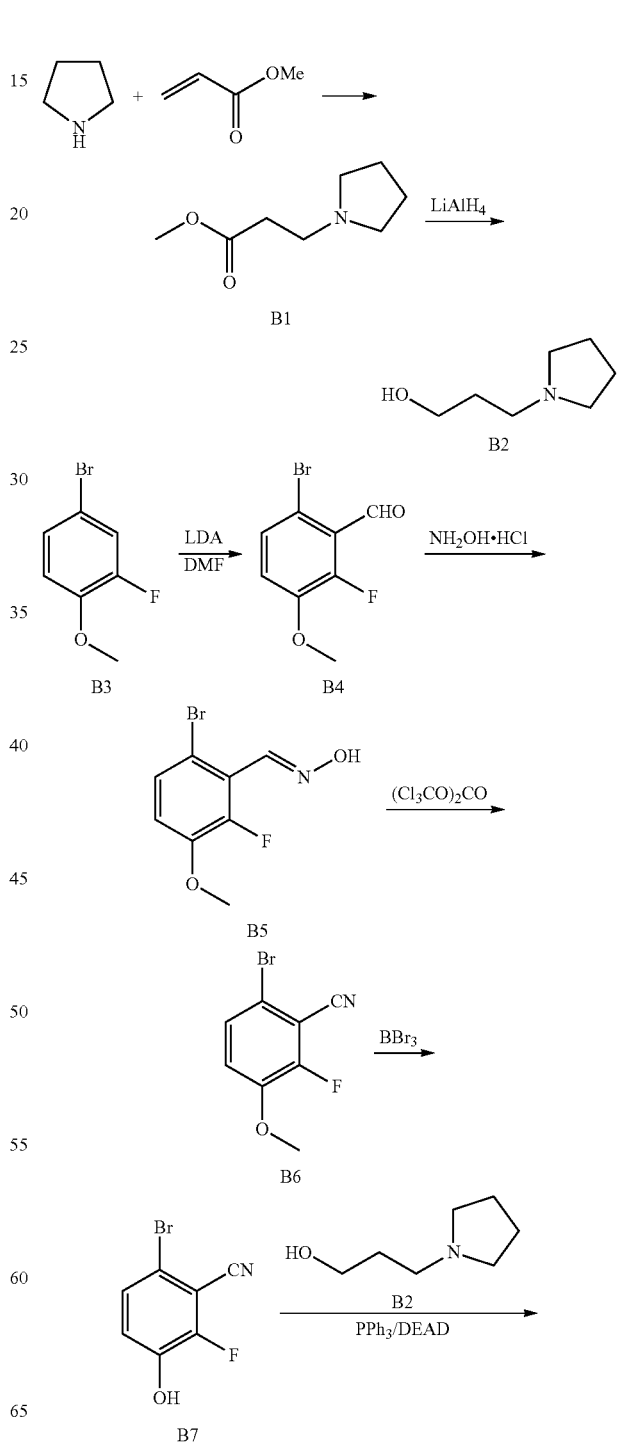

-continued

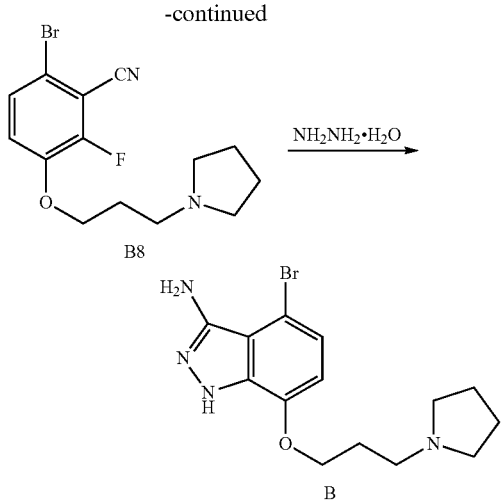

2.1 Synthesis of Compound B1

Under the condition of ice-water bath, 36.3 g methyl acrylate was dissolved in 300 mL dichloromethane and then added into a 500 mL three-necked flask. The solution was kept at temperature 0-5° C. and 30 g pyrrolidine was added into the solution, then the resulted solution was heated to room temperature. After 2 hours, the reaction had completed by checking by TLC. The system was vacuum concentrated to remove methylene chloride to give 64 g colorless oily substance, i.e. compound B1, 96% yield. $^1$H-NMR (400 MHz, DMSO-d6) (ppm) 1.60-1.70 (m, 4H), 2.41-2.48 (m, 6H), 2.62-2.65 (m, 2H), 3.59 (s, 3H).

2.2 Synthesis of Compound B2

Under the condition of ice-salt bath, 300 mL tetrahydrofuran was added into a 500 mL three-necked flask, and then 8 g LiAlH4 was portionwise added with keeping the temperature not exceeding 0° C. The solution of 30 g compound 81 dissolved in 30 mL THF was dropwise added, and gas released violently. The system was naturally warmed to room temperature. After 2 hours, the reaction had completed by checking by TLC. 100 mL THF solution containing 12% water was added, and gas released violently. Then 30 mL of 15% NaOH solution was added, and gas released a little. The system was added with 40 mL water, and then extracted with 70 mL dichloromethane for three times. The organic phases were merged, washed with salt water, dried with anhydrous sodiumsulfate, and concentrated to dryness to give 16 g yellow solid, i.e. compounds 92, 65% yield. $^1$H-NMR (400 MHz, CDCl3) (ppm) 1.70-1.79 (m, 6H), 2.56-2.59 (m, 4H), 2.72-2.75 (m, 2H), 3.81 (t, J=5.6, 2H).

2.3 Synthesis of Compound B4

In 1 L three-necked flask, 39.4 g diisopropylamine was dissolved in 100 mL THF and cooled to −5° C. Under nitrogen protection, 148.6 mL of 2.5M n-butyllithium solution was added into the system, and the solution was stirred at 0° C. for 1 h, and then cooled to −70° C. The solution of 69.2 g 2-fluoro-4-bromoanisole dissolved in 450 mL THF was added and then stirred for 2 h. The solution of 49.3 g DMF dissolved in 150 mL THF was dropwise added and stirred for 2 hours. The reaction had completed by checking by TLC. 4 L sodium bicarbonate solution was added, and the solution was extracted by 1 L ethyl acetate for two times. The organic phases were merged, washed with saturated saline solution, dried by anhydrous sodiumsulfate, and concentrated to remove most of ethyl acetate. 300 mL petroleum ether was added with stirring, and the system was stirred for 30 min filtered to give a white floccule which was dried to give 53 g compound B4, 67.4% yield. $^1$H-NMR (400 MHz, DMSO-d6) (ppm) 3.89 (s, 3H), 7.40-7.44 (m, 1H), 7.56-7.58 (m, 1H), 10.18 (s, 1H).

2.4 Synthesis of Compound B5

Under mechanical stirring, 52.7 g compound B4, 15.8 g Na$_2$CO$_3$, 1000 mL methanol and 500 mL water were added into a 2 L single neck flask, respectively. After stirring evenly, 17.3 g hydroxylamine hydrochloride was slowly added in. After stirring and reacting for 2 h, the reaction had completed by checking by TLC. 1.2 L water was added, and the solution was extracted with 1.5 L ethyl acetate for two times. The organic phases were merged, washed with saturated saline solution, dried by anhydrous sodiumsulfate, concentrated to remove most of solvent, and mashed with petroleum ether to give a white solid, i.e. 54 g the compound B5, 100% yield. $^1$H-NMR (400 MHz, DMSO-d6) (ppm) 3.86 (s, 3H), 7.18 (t, J=8.8, 1H), 7.47-7.50 (m, 1H), 8.13 (s, 1H), 11.86 (s, 1H).

2.5 Synthesis of Compound B6

44.5 g compound 135 and 250 mL DMF were added into a 500 mL three-necked flask. Under the condition of ice water bath and keeping temperature <35° C., 31.9 g triphosgene was slowly added and the reaction was violent and outgassing. After stirring and reacting for 30 min, the reaction had completed by checking by HPLC. The reaction solution was added into 1 L water and filtered, and the solid phase was dissolved in 450 mL methylene chloride and concentrated to remove most of solvent, and mashed with petroleum ether to give 39 g white solid powder, i.e. compound B6, 95% yield. $^1$H-NMR (400 MHz, CDCl$_3$) (ppm) 3.94 (s, 3H), 7.10 (t, J=8.8, 1H), 7.40-7.43 (m, 1H).

2.6 Synthesis of Compound B7

Keeping the temperature at −10° C. and under nitrogen protection, 33.6 g compound B6 and 240 mL dichloromethane were added into a 1 L three-necked flask. The solution of 54.8 g BBr$_3$ dissolved in 240 mL dichloromethane was dropwise added. After the adding finished, the solution naturally warmed to room temperature and reacted for 24 hours, and 1N BBr$_3$ was added. The system was stirred and reacted for 24 hours, the reaction had completed by checking by TLC. Under condition of ice-water bath, 3N hydrochloric acid was added, and lots of gas was released and heat was released violently. The system was extracted with 800 mL dichloromethane for two times, washed with saturated saline solution and concentrated to remove most of solvent, mashed with PE (petroleum ether) to give 29 g light green solid powder, i.e. compound B7, 92% yield. $^1$H-NMR (400 MHz, DMDO-d6) (ppm) 7.23-7.27 (m, 1H), 7.49-7.51 (m, 1H), 11.06 (s, 1H).

2.7 Synthesis of Compound B8

28.5 g compound B7, 16 g compound 82, 51.9 g triphenylphosphine and 500 mL THF were added into a 1 L three-necked flask under nitrogen protection, respectively, and cooled to 0° C. Keeping temperature <0° C., 34.5 g DEAD was dropwise added within 30 min. After adding was completed, the system was naturally warmed to room temperature and reacted for 2.5 hours. The reaction had substantially completed by checking by TLC. The solution was concentrated to remove the solvent to dryness, added with 200 mL ether and frozen overnight. The resulted system was filtered, and the mother liquor was concentrated and purified by column chromatography to give 33 g yellow oily substance, i.e. compound B8, 77% yield. $^1$H-NMR (400 MHz, DMDO-d6) (ppm) 1.66-1.70 (m, 2H), 1.89-1.95 (m, 2H), 2.48-2.58 (m, 8H), 4.17 (t, J=6.0, 2H), 7.51-7.56 (m, 1H), 7.63-7.65 (m, 1H).

2.8 Synthesis of Segment B 90 g compound B8, 81.2 g of 85% hydrazine hydrate and 230 mL n-butanol were added into a. 500 mL single neck flask. The solution was heated to 100° C. and refluxed overnight. The reaction had substantially completed by checking by TLC. The n-butanol was concentrated to dryness, and 1 L water was added. The resulted system was extracted with DCM (Dichloromethane) (500 mL×6). The organic phases were merged, washed with saturated saline solution, concentrated to dryness and mashed with PE to give 40 g yellow solid. 120 mL methanol was added. The system was heated to 50° C., stirred for 1 hour, and then cooled to room temperature, filtered and dried to give 38 g white solid, i.e., segment B, 41% yield, purity greater than 99%. $^1$H-NMR (400 MHz, DMDO-d6) (ppm) 1.74 (m, 4H), 1.98 (m, 2H), 2.61-2.75 (m, 6H), 4.13 (m, 2H), 5.08 (s, 2H), 6.62 (d, 2H), 6.94 (d, 2H), 12.06 (s, 1H).

Example 3

Synthesis of Segment C

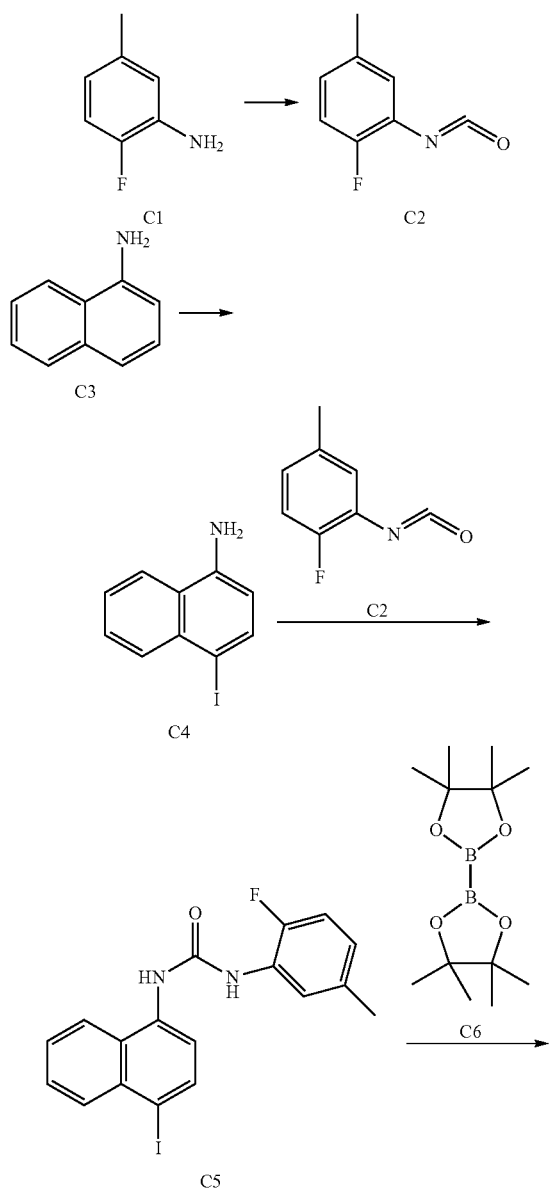

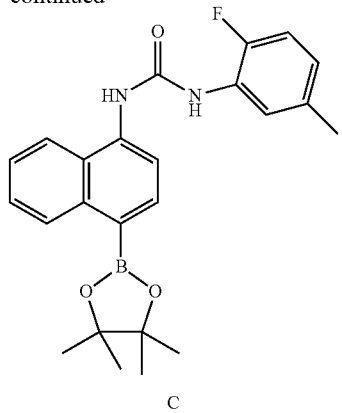

C

3.1 Synthesis of Compound C2

4.9 g triphosgene and 25 mL methylbenzene were added into a 500 mL single-neck flask respectively, and stirred to dissolve to be clarified at room temperature. The solution of 3.75 g 2-fluoro-5-methylaniline dissolved in 5 mL methylbenzene was dropwise added, and during dropwise adding, lots of solid was produced. After adding was complete, the system was stirred for 30 minutes at room temperature, and then heated to reflux and react for 3 hours (during refluxing, the reaction solution was clear). The resulted solution was cooled, vacuum-concentrated to dryness to give 3.8 g colorless oily substance, i.e. compound C2, which was directly used in the next step without further processing. $^1$H-NMR (400 MHz, DMSO-d6) (ppm) 7.06-7.12 (m, 2H), 7.22-7.27 (m, 1H).

3.2 Synthesis of Compound C4

50 g 1-naphthylamine, 250 mL dioxane and 250 mL pyridine were added in a 1 L three-necked flask, respectively, stirred evenly and cooled to −5~0° C. It was added 132 g iodine was portionwise added in and during charging, and the temperature was controlled to be below 0° C. After charging finished, the system was stirred and reacted at 0~5° C. for 4~5 hours. The raw material had reacted completely by checking by TLC. 300 mL of 5% sodium thiosulfate aqueous solution was added to quench the reaction. The system was extracted by dichloromethane (250 mL×3). The combined organic phases were merged, washed with water (250 mL×1), washed by saturated saline solution (250 mL×1), dried by anhydrous sodiumsulfate, and vacuum-concentrated to dryness to give a dark purple oily substance which was recrystallized with dichloromethane and petroleum ether to give a light purple solid, i.e. compound C4, 40 g. $^1$H-NMR (400 MHz, DMSO-d6) (ppm) 6.01 (s, 2H), 6.52 (d, 1H), 7.53-7.57 (m, 2H), 7.74 (d, 1H), 7.83 (d, 1H), 8.07 (d, 1H).

3.3 Synthesis of Compound C5

7.12 g compound C4 and 50 mL dichloromethane were added into a 100 mL single-neck flask and dissolved to be clarified. 4.0 g compound C2 was dropwise added at room temperature and the resulted solution was stirred at room temperature overnight to produce a lot of solid. The system was pumping filtered, and the filtered cake was drip washed with petroleum ether, and pumped to dryness to give 12.5 g grey white solid, i.e. compound C5.

3.4 Synthesis of Segment C 12.5 g compound C5, 9.1 g compound C6, 0.075 g tetrakis(triphenylphosphine) palladium, 12.3 g potassium carbonate and 100 mL DMSO were added into a 250 mL single neck flask, respectively. Under nitrogen protection, the resulted solution was heated to 80~85° C. and reacted for 3-4 hours. The reaction had completed by checking by TLC. The system was cooled, and 150 mL water was added to quench the reaction. The solution was extracted with ethyl acetate (150 mL×3). The organic layers were washed with saturated saline solution (150 mL×2), dried by anhydrous sodiumsulfate, decolorized with activated carbon, and concentrated to remain about 200 mL ethyl acetate, crystallized at freeze, filtered and recrystallized with petroleum ether and ethyl acetate to give 6.8 g gray solid powder, i.e. segment C. $^1$H NMR (400 MHz, DMSO-d6) (ppm) 1.38 (s, 12H), 2.30 (s, 3H), 6.83 (t, J=5.6, 1H), 7.12-7.16 (m, 1H), 7.61 (m, 1H), 7.97 (d, 1H), 8.10 (d, 1H), 8.20-8.24 (m, 2H), 8.74 (d, 1H), 9.13 (s, 1H), 9.32 (s, 1H).

Example 4

Synthesis of Segment D

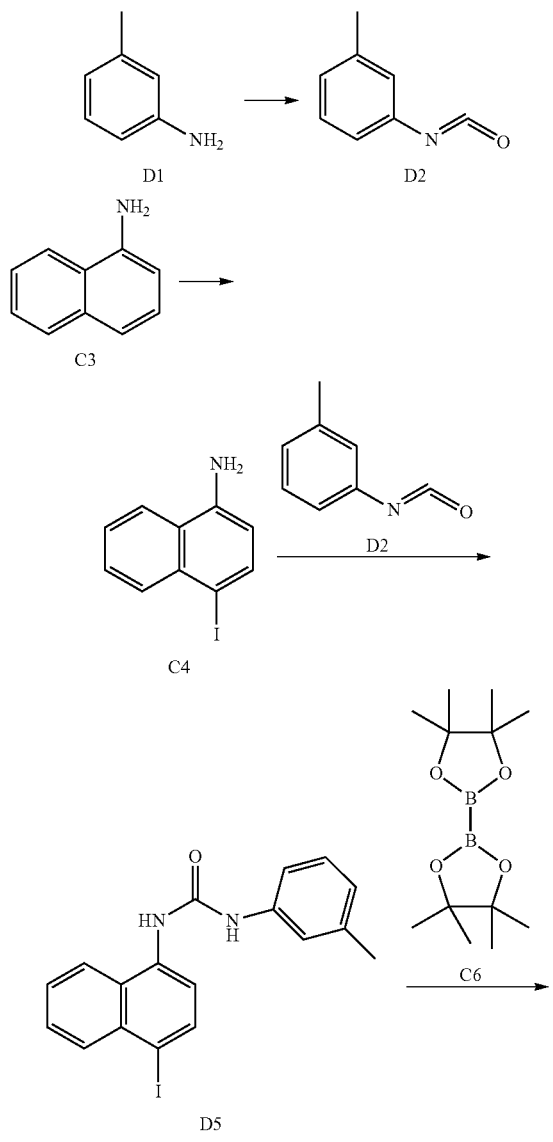

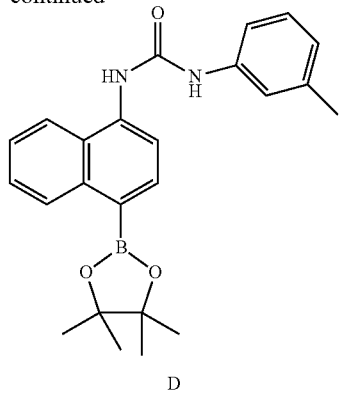

D

4.1 Synthesis of Compound D2

32.6 g triphosgene and 200 mL methylbenzene were added into a 500 mL single-neck flask, respectively, and stirred to dissolve to be clarified at room temperature. The solution of 21.43 g m-methylaniline dissolved in 10 mL methylbenzene was dropwise added, and during dropwise adding, lots of solid was produced. After adding was complete, the system was stirred for 30 minutes at room temperature, and then heated to reflux and react for 3 hours (during refluxing, the reaction solution was clear). The resulted solution was cooled, vacuum-concentrated to dryness to give 41 g brown oily substance, which was reduced-pressure distilled under oil pump high vacuum to give 16 g colorless and transparent oily substance, i.e. compound D2. $^1$H-NMR (400 MHz, DMSO-d6) (ppm) 7.02-7.07 (m, 2H), 7.24-7.28 (m, 1H).

4.2 Synthesis of Compound D5

3 g compound C4 and 15 mL dichloromethane were added into a 50 mL single-neck flask and stirred to dissolve to be clarified. 1.5 g compound D2 was dropwise added at room temperature and the resulted solution was stirred and reacted at room temperature overnight to produce a lot of solid. The system was pumping filtered, and the filtered cake was drip washed with petroleum ether, and pumped to dryness to give 4 g grey white solid, i.e. compound D5.

4.3 Synthesis of Segment D 10.4 g compound D5, 7.9 g compound C6, 0.06 g tetrakis(triphenylphosphine) palladium, 10.7 g potassium carbonate and 70 mL DMSO were added into a 100 mL single neck flask, respectively. Under nitrogen protection, the resulted solution was heated to 80~85° C. and reacted for 4~5 hours. The reaction had completed by checking by TLC. The system was cooled, and 200 mL water was added to quench the reaction. The solution was extracted with ethyl acetate (200 mL×3). The organic layers were washed with saturated saline solution (200 mL×1), dried by anhydrous sodiumsulfate, decolorized with activated carbon, and concentrated to remain about 200 mL ethyl acetate, crystallized at freeze, filtered and recrystallized with petroleum ether and ethyl acetate to give 5.5 g purple solid powder, i.e. segment D, 53% yield. $^1$H-NMR (400 MHz, DMSO-d6) (ppm) 1.37 (s, 12H), 2.31 (s, 3H), 6.82 (m, 1H), 7.19-7.62 (m, 5H), 7.96-7.99 (m, 1H), 8.18-8.22 (m, 1H), 8.76-8.77 (m, 1H), 8.95 (s, 1H), 9.11 (s, 1H).

Example 5

Synthesis of Compound (III)

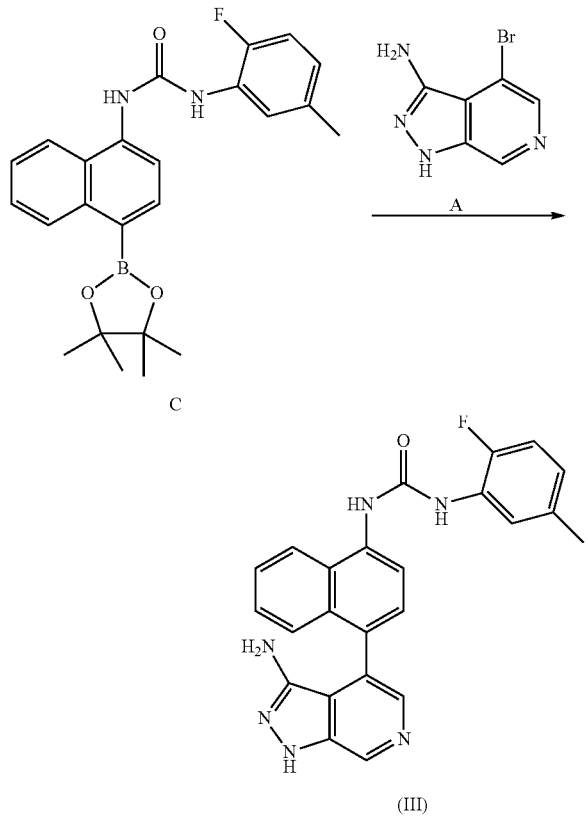

(III)

Example 6

Synthesis of Compound (IV)

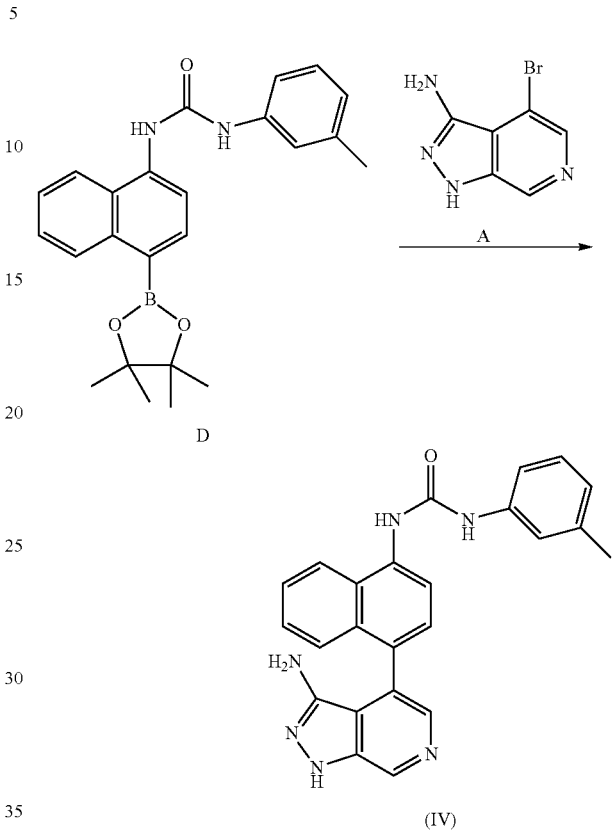

(IV)

Compound C (8.4 g, 20 mmol), compound A (5.1 g, 24 mmol), potassium carbonate (8.28 g, 60 mmol), tetrakis (triphenylphosphine) palladium (0.4 g), ethylene glycol dimethyl ether (240 mL) and water (60 mL) were added into a 500 mL single-neck flask, respectively, and nitrogen displacement was executed for 3 times. The system was heated to 85~90° C. stirred and reacted for 16 hours. The reaction had completed by checking by TLC. The system was cooled, and 500 mL water was added to quench the reaction. The solution was extracted with ethyl acetate (500 mL×3). The organic layers were washed with saturated saline solution (300 mL×2), dried by anhydrous sodiumsulfate, decolorized with activated carbon, and concentrated to give 6.5 g brown oily substance which was purified by column chromatography to give 3 g light yellow solid product, i.e. compound (III), 35% yield, HPLC purity greater than 98%. $^1$H-NMR (400 MHz, DMSO-d6) (ppm) 2.30 (s, 3H), 4.09 (s, 2H), 6.84 (t, J=9.6, 1H), 7.15 (t, J=8.0, 1H), 7.51 (t, J=8.4, 1H), 7.66-7.70 (m, 1H), 7.97 (s, 1H), 8.11 (t, J=6.4, 1H), 8.25 (d, 1H), 8.31 (d, 1H), 8.87 (s, 1H), 9.11 (s, 1H), 9.34 (s, 1H), 12.32 (w, 1H).

$^{13}$C-NMR (100 MHz, DMSO-d6) (ppm) 21.3, 114.9, 115.1, 116.5, 116.8, 121.4, 122.3, 123.1, 126.1, 126.4, 127.2, 127.6, 128.0, 128.3, 128.5, 132.7, 134.0, 135.3, 137.5, 138.3, 148.7, 149.6, 152.0, 153.1.

By detection, in compound (III), C content was 67.38%, H content was 4.62%, and molecular formula was $C_{24}H_{19}FN_6O$ (by calculating, C content is 67.60%, H content is 4.49%).

LCMS: 409.2 (M+H).

Compound D (8.05 g, 20 mmol), compound A (5.1 g, 24 mmol), potassium carbonate (8.28 g, 60 mmol), tetrakis (triphenylphosphine)palladium (0.4 g), ethylene glycol dimethyl ether (240 mL) and water (60 mL) were added into a 500 mL single-neck flask, respectively, and nitrogen displacement was executed for 3 times. The system was heated to 85~90° C., stirred and reacted for 16 hours. The reaction had completed by checking by TLC. The system was cooled, and 500 mL water was added to quench the reaction. The solution was extracted with ethyl acetate (500 mL×3). The organic layers were washed with saturated saline solution (300 mL×2), dried by anhydrous sodiumsulfate, decolorized with activated carbon, and concentrated to give 7.4 g brown oily substance which was purified by column chromatography to give 3.43 g light yellow solid product, i.e. compound (IV), 42% yield, HPLC purity greater than 98%. $^1$H-NMR (400 MHz, DMSO-d6) (ppm) 2.31 (s, 3H), 4.09 (s, 2H), 6.82 (d, 1H), 7.20 (t, J=8.0, 1H), 7.33-7.66 (m, 6H), 7.97 (s, 1H), 8.22 (d, 1H), 8.37 (d, 1H), 8.86 (s, 1H), 9.17 (s, 1H), 9.43 (s, 1H), 12.33 (w, 1H).

$^{13}$C-NMR (100 MHz, DMSO-d6) (ppm) 21.7, 115.6, 116.2, 116.5, 118.9, 122.9, 123.1, 126.0, 126.2, 126.3, 127.1, 127.8, 128.2, 128.3, 129.1, 132.7, 133.9, 136.0, 137.4, 138.3, 140.6, 148.7, 153.7.

By detection, in compound (IV). C content was 70.32%, H content was 5.02%, and molecular formula was $C_{24}H_{20}N_6O$ (by calculating, C content is 70.57%, H content is 4.94%).

LCMS: 409.2 (M+H).

Example 7

Synthesis of Compound (V)

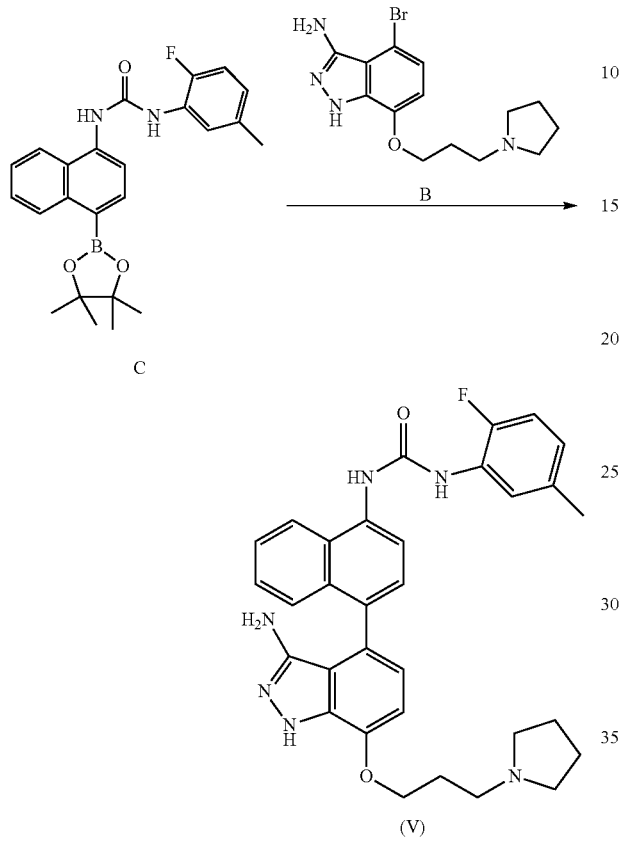

Compound C (8.4 g, 20 mmol), compound B (8.14 g, 24 mmol), potassium carbonate (8.28 g, 60 mmol), tetrakis(triphenylphosphine)palladium (0.4 g), ethylene glycol dimethyl ether (240 mL) and water (60 mL) were added into a 500 mL single-neck flask, respectively, and nitrogen displacement was executed for 3 times. The system was heated to 85~90° C., stirred and reacted for 16 hours. The reaction had completed by checking by TLC. The system was cooled, and 500 mL water was added to quench the reaction. The solution was extracted with ethyl acetate (500 mL×3). The organic layers were washed with saturated saline solution (300 mL×2), dried by anhydrous sodiumsulfate, decolorized with activated carbon, and concentrated to give 6.2 g brown oily substance which was purified by column chromatography to give 3.53 g offwhite solid product, i.e. compound (V), 32% yield, HPLC purity greater than 98%.

$^1$H-NMR (400 MHz, DMSO-d6) (ppm) 1.85-1.88 (m, 4H), 2.12-2.30 (m, 4H), 3.08-4.27 (m, 10H), 6.73-6.85 (m, 3H), 7.15 (m, 1H), 7.39-7.64 (m, 4H), 8.09-8.30 (m, 4H), 9.11 (s, 1H), 9.31 (s, 1H), 11.97 (w, 1H).

$^{13}$C-NMR (100 MHz, DMSO-d6) (ppm) 21.3, 23.4, 26.9, 28.4, 30.9, 52.1, 53.8, 60.4, 114.9, 115.1, 116.0, 117.1, 118.5, 121.4, 122.2, 123.1, 125.8, 126.2, 126.7, 126.9, 127.6, 132.1, 133.0, 133.8, 134.0, 134.5, 143.9, 149.1, 149.6, 152.0, 153.2.

By detection, in compound (V), C content was 69.38%, H content was 6.20%, and molecular formula was $C_{32}H_{33}FN_6O_2$ (by calculating, C content is 69.55%, H content is 6.02%).

LCMS: 553.2 (M+H).

Example 8

Synthesis of Compound (VI)

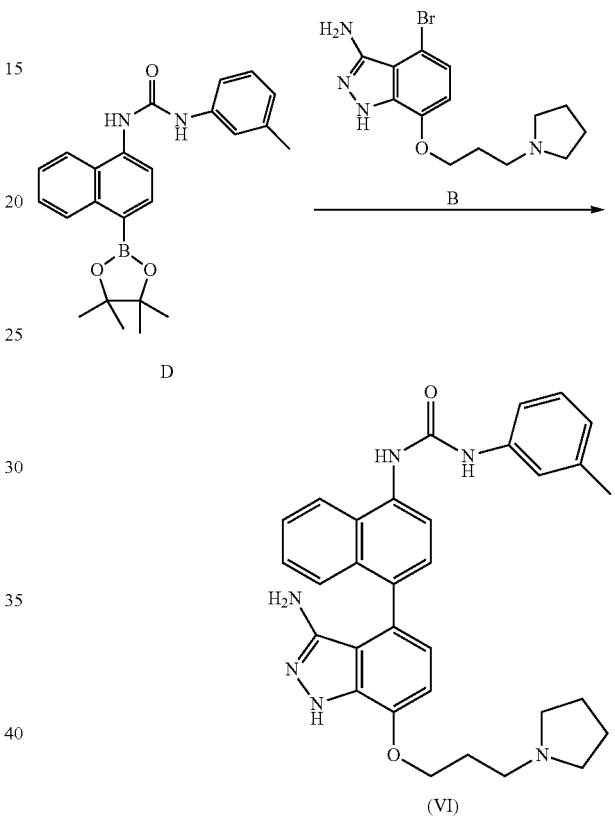

Compound D (8.05 g, 20 mmol), compound B (8.14 g, 24 mmol), potassium carbonate (8.28 g, 60 mmol), tetrakis(triphenylphosphine)palladium (0.4 g), ethylene glycol dimethyl ether (240 mL) and water (60 mL) were added to a 500 mL single-neck flask, respectively, and nitrogen displacement was executed for 3 times. The system was heated to 85~90° C., stirred and reacted for 16 hours. The reaction had completed by checking by TLC. The system was cooled, and 500 mL water was added to quench the reaction. The solution was extracted with ethyl acetate (500 mL×3). The organic layers were washed with saturated saline solution (300 mL×2), dried by anhydrous sodiumsulfate, decolorized with activated carbon, and concentrated to give 7.4 g brown oily substance which was purified by column chromatography to give 4.06 g offwhite solid product. i.e. compound (VI), 38% yield. HPLC purity greater than 98%.

$^1$H-NMR (400 MHz, DMSO-d6) (ppm) 1.98-2.24 (m, 4H), 2.24-2.31 (m, 4H), 3.44 (w, 2H), 3.55-3.57 (m, 4H), 4.26 (m, 2H), 4.28 (m, 2H), 6.74 (d, 1H), 6.81 (d, 1H), 6.87 (d, 1H), 7.19 (t, J=8.0, 1H), 7.34-7.62 (m, 6H), 8.15 (d, 1H), 8.40 (d, 1H), 9.23 (s, 1H), 9.60 (s, 1H), 10.47 (w, 1H), 11.93 (s, 1H).

$^{13}$C-NMR (100 MHz, DMSO-d6) (ppm) 21.7, 23.2, 26.0, 51.9, 53.9, 65.4, 114.3, 115.8, 117.1, 119.1, 121.0, 122.5, 123.1, 126.0, 126.2, 126.3, 126.7, 126.8, 127.7, 129.2, 131.8, 133.0, 133.8, 134.8, 138.5, 140.3, 143.7, 149.2, 153.5.

By detection, in compound (VI). C content was 71.75%, H content was 6.55%, and molecular formula was C$_{32}$H$_{34}$N$_6$O$_2$ (by calculating, C content is 71.89%, H content is 6.41%).

LCMS: 535.3 (M+H).

Example 9

Synthesis of Compound (VII)

Step 1: Synthesis of Intermediate E2

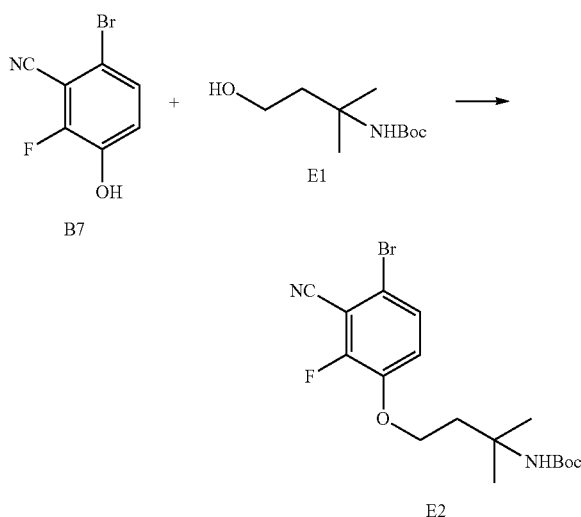

Under nitrogen protection and at room temperature (10-15° C.), compound B7, triphenylphosphine and THF (55 mL) were added into a 200 mL three-necked flask, respectively, and stirred. DBAD (di-tert-butyl azodicarboxylate) was added under nitrogen protection, and heat was released. The resulted solution was stirred for 15 minutes at room temperature. The solution of compound E1 (commercially purchased) dissolved in 20 mL THF was dropwise added, and the adding lasted for 7 hours. And then the system was stirred at room temperature (10-15° C.) for 15 hours. The resulted solution was vacuum concentrated at 40° C. to dryness, and then purified by column chromatography (PE/EA=6/1) to give 12.8 g oily substance, which was shown to be intermediate E2 via NMR.

Step 2: Synthesis of Intermediate E3

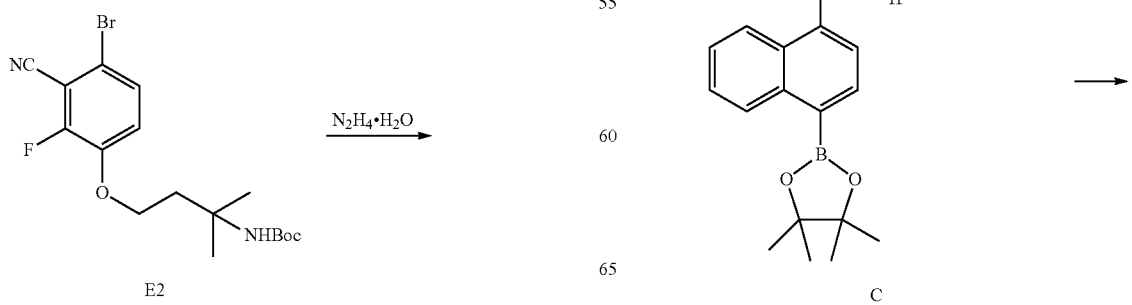

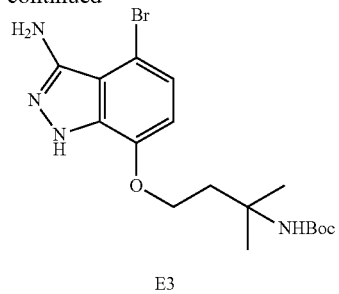

Compound E2 (12 g) prepared according to step 1 was added with 50 mL n-butanol and 6.25 g of 80% hydrazine hydrate. The solution was heated to 100° C., stirred for 15 hours, vacuum-concentrated to remove n-butanol. 50 mL dichloromethane was added. The resulted system was washed with saline solution and dried by anhydrous sodiumsulfate. Sodium sulfate was removed by filtration and 5 mL trifluoroacetic acid was added. The solution was stirred for 20 minutes at room temperature and gas was released. The system was vacuum concentrated to dryness. Sodium carbonate aqueous solution was added into the residue to adjust the pH to 9. The solution was extracted by TBME for 3 times. The organic phases were merged, washed with saline solution, dried by sodium sulfate, filtered, and concentrated to give 14 g yellow oily substance which was purified by column chromatography (firstly, eluting impurities with small polarity such as triphenylphosphine via PE/EA=6/1, then gradually increasing the eluent polarity, and at last eluting the target product at DCM/MeOH=5/1), concentrated to dryness and mashed with 10 mL mixed solvent of PE/EA=10/1 to give 4.5 g off-white solid, HPLC purity greater than 95%, which was shown to be the target intermediate E3 via NMR.

Step 3: Synthesis of Intermediate E5

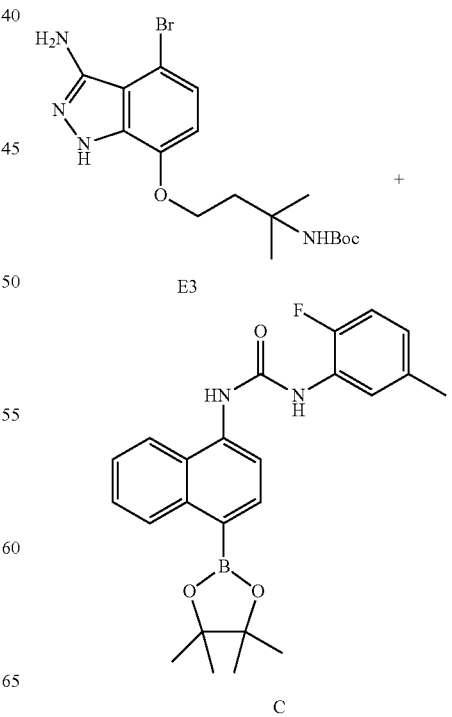

25

-continued

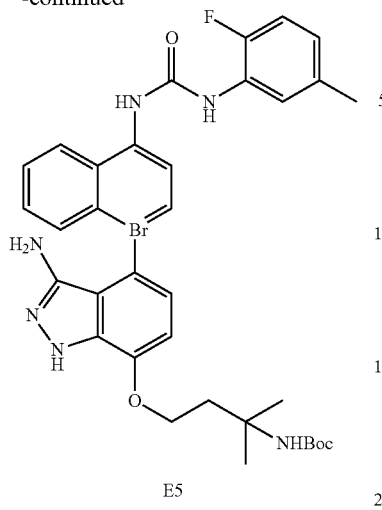

E5

Compound E3 prepared according to step 2, compound C and Pd catalyst were added into a 50 mL three-necked flask respectively, and nitrogen displacement was executed for 3 times. THF and potassium carbonate aqueous solution were added via an injector. The solution was heated to 80° C. and stirred for 15 hours in an oil bath. Water was added to quench the reaction. The solution was extracted with ethyl acetate for 3 times, and the organic phases were merged, washed with saline solution, dried by sodium sulfate, filtered through diatomite, concentrated to dryness, and purified by column chromatography (DCM/MeOH=20/1~10/1), purified again by column chromatography depending on the colour and purity, to give a product at point (DCM/MeOH=20/1~10/1, Rf=0.2) which was concentrated to dryness and give 0.65 g substance, i.e. intermediate E5, which was directly used in the next reaction.

Structure of Pd Catalysts:

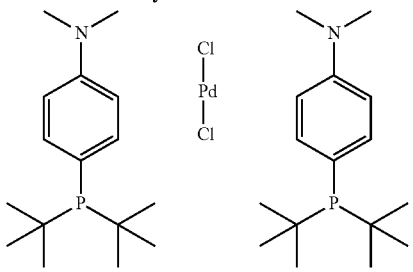

Step 4: Synthesis of Compound (VII)

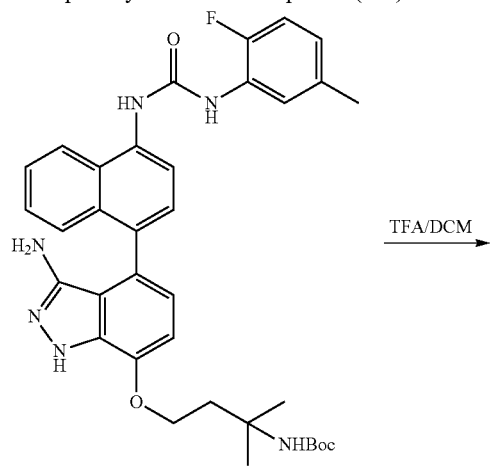

E5

26

-continued

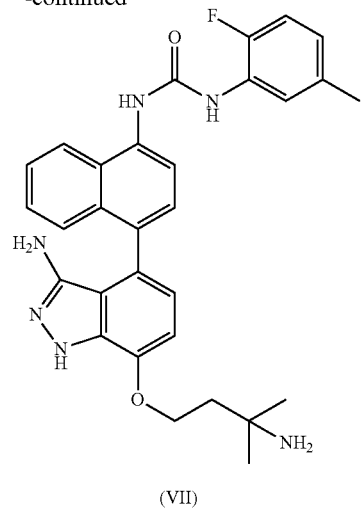

(VII)

0.67 g compound E5 prepared according to step 3 was added with 20 mL dichloromethane. 8 mL trifluoroacetic acid was added at room temperature and the resulted solution was stirred for 15 hours at room temperature. TLC indicated that the reaction was complete. The solution was vacuum concentrated to dryness, and potassium carbonate aqueous solution was added into the residue to adjust pH to be >10. The solution was extracted with dichloromethane/methanol=2/1, dried by sodium sulfate, filtered to remove sodium sulfate, concentrated to dryness, and purified by column chromatography (DCM/MeOH=20/1~2/1) to collect product at point (DCM/MeOH=5/1, Rf=0.2) which was concentrated to give 0.4 g light yellow solid, which had single point in TLC test, however the HPLC purity of which was only 87%, and thus which had an impurity with large polarity. 200 mg product sample was purified by preparative chromatography to give 105 mg product, which had HPLC purity 99.0% and was confirmed to be target product compound (VII) via NMR.

$^1$H-NMR (400 MHz, DMSO-d6) (ppm) 1.15 (s, 6H), 1.92 (t, J=7.2, 2H), 2.30 (s, 3H), 3.78 (s, 2H), 4.32 (t, J=7.2, 2H), 6.66 (d, 1H), 6.73 (d, 1H), 6.82 (d, 1H), 6.89 (d, 1H), 6.95 (d, 1H), 7.13-7.18 (m, 1H), 7.41-7.66 (m, 4H), 8.10 (d, 1H), 8.16 (d, 1H), 8.27 (d, 1H), 9.08 (s, 1H), 9.28 (s, 1H), 11.87 (w, 1H).

$^{13}$C-NMR (100 MHz, DMSO-d6) (ppm) 21.3, 31.0, 42.9, 49.1, 65.9, 103.8, 106.5, 107.7, 113.1, 114.9, 117.2, 121.1, 121.9, 123.1, 125.4, 126.3, 126.7, 127.7, 132.3, 133.0, 133.9, 134.0, 134.4, 134.9, 144.3, 149.0, 149.6, 152.0, 153.2.

By detection, in compound (VII), C content was 68.53%, H content was 5.98%, N content was 15.85%, and molecular formula was $C_{30}H_{31}FN_6O_2$ (by calculating, C content is 68.42%, H content is 5.93%, and H content is 15.96%).

LCMS: 527.3 (M+H).

Example 10

Synthesis of Compound (VIII)

Step 1: Synthesis of Intermediate E4

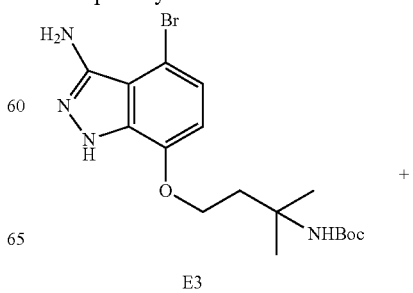

E3

Step 2: Synthesis of Compound (VIII)

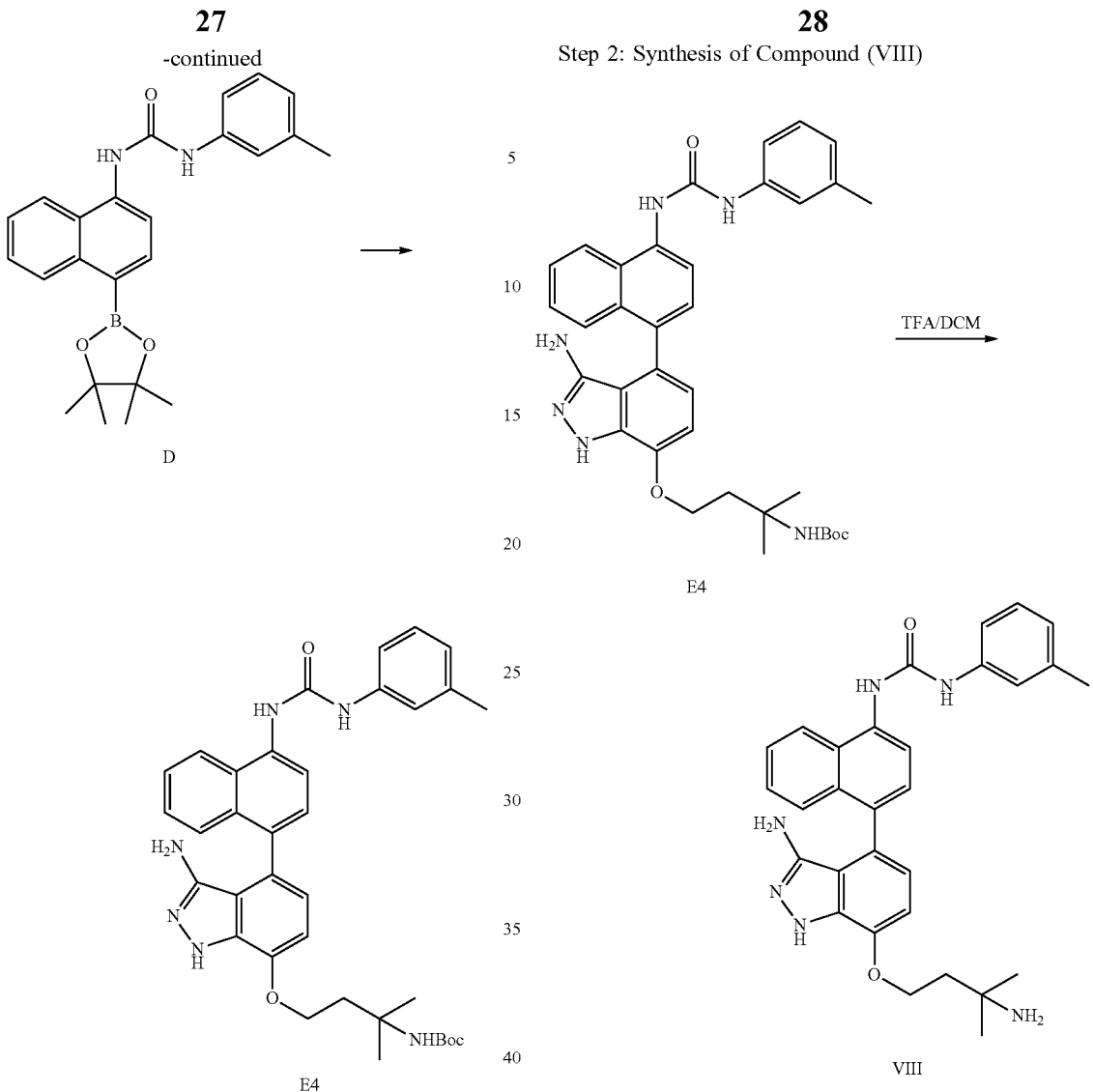

Compound E3, compound D and Pd catalyst (the same as in Example 9) were added into a 50 mL three-necked flask respectively, and nitrogen displacement was executed for 3 times. THF and potassium carbonate aqueous solution were added via an injector. The solution was heated to 80° C. and stirred for 15 hours in an oil bath. Water was added to quench the reaction. The solution was extracted with ethyl acetate for 3 times, and the organic phases were merged, washed with saline solution, dried by sodium sulfate, filtered through diatomite, concentrated to dryness, and purified by column chromatography (DCM/MeOH=20/1~10/1), purified again by column chromatography depending on the colour and purity, to give a product at point (DCM/MeOH=20/1~10/1. Rf=0.2) which was concentrated to dryness and mashed with PE/EA=2/1 to give 0.87 g offwhite solid, i.e. intermediate E4.

Compound E4 (0.77 g) prepared according to step 1 was added with 10 mL dichloromethane, and a lot of solid was undissolved. 5 mL trifluoroacetic acid was added at room temperature and the solution was dissolved to be clarified. The system was stirred for 15 hours at room temperature. TLC indicated that the reaction was complete. The solution was vacuum concentrated to dryness, and potassium carbonate aqueous solution was added into the residue to adjust pH to be >10. The solution was extracted with dichloromethane/methanol=2/1, dried by sodium sulfate, filtered to remove sodium sulfate, concentrated to dryness, and purified by column chromatography (DCM/MeOH=20/1-2/1) to collect product at point (DCM/MeOH=5/1, Rf=0.2) which was concentrated to give 0.6 g grey solid. The solid was confirmed to be target product compound (VIII) via NMR, and purified again by column chromatography to give 450 mg offwhite target product. HPLC purity 97.2%.

$^1$H-NMR (400 MHz, DMSO-d6) (ppm) 1.40 (s, 6H), 2.17 (t, J=6.4, 2H), 2.31 (s, 3H), 3.81 (s, 2H), 4.35 (t, J=6.4, 2H), 6.75 (d, 1H), 6.81 (d, 1H), 6.90 (d, 1H), 7.18 (d, 1H), 7.21 (d, 1H), 7.33-7.63 (m, 5H), 7.94 (w, 2H), 8.12 (d, 1H), 8.30 (d, 1H), 9.12 (s, 1H), 9.38 (s, 1H), 11.84 (w, 1H).

$^{13}$C-NMR (100 MHz, DMSO-d6) (ppm) 21.7, 26.1, 39.1, 53.2, 64.1, 106.4, 114.3, 115.9, 117.5, 119.1, 121.1, 122.5, 123.0, 125.9, 126.2, 126.7, 126.8, 127.7, 129.2, 131.9, 133.0, 133.7, 134.8, 138.4, 140.4, 149.1, 153.7, 159.1.

By detection, in compound (VIII), C content was 70.95%, H content was 6.55%, N content was 16.35%, and molecular formula was $C_{30}H_{32}N_6O_2$ (by calculating, C content is 70.84%, H content is 6.34%, and H content is 16.53%).

LCMS: 509.3 (M+H).

In Vitro Test of Inhibition of Naphthalurea Derivatives According to the Present Invention on the Activity of VEGFR2 and PDGFR-β Receptor Tyrosine Kinase 1. Experiment Method Enzyme-Linked Immunosorbent Assay (ELISA)

Main Instruments

Tunable wavelength type microplate reader (Molecular Devices SPECTRAMAX190)

Main Reagents

Tested samples: a series of instantiation compounds II-VI of Embodiment 1, diluted to desired concentrations with solvent DMSO before use;

Control group: Sorafenib (Su11248);

Tyrosine kinases VEGFR2 (KDR), c-Kit expressed by utilizing the insect baculovirus expression system and affinity purified by Ni-NTA column, and met the experimental requirements by detection;

Tyrosine kinase PDGFR-β (MILLIPORE);

Kinase reaction substrate Poly(Glu, Tyr, 4:1) (SIGMA);

Anti-phosphotyrosine monoclonal antibody PY99 (SANTA CRUZ);

Horseradish peroxidase-labeled goat anti-rabbit IgG (CALABIOCHEM);

ATP, DTT, OPD (AMRESCO);

Enzyme labeled plate (CORNING);

Sorafenib (LC LABORATORIES);

Other reagents made in China.

Experimental Procedures (1) Kinase reaction substrate Poly(Glu, Tyr, 4:1) was diluted to 20 μg/ml with potassium ion-free PBS, and enzyme labeled plate was coated by the substrate, reacted at 37° C. for 12-16 h, and then the liquid in holes was removed.

(2) Enzyme labeled plate was washed with T-PBS for three times, 10 min each time.

(3) Enzyme labeled plate was dried at 37° C. in a dryer.

(4) The tested samples were added into holes of the coated enzyme labeled plate:

The tested samples were firstly formulated to be a $10^{-2}$ M stock solution with DMSO, and then diluted to required concentration with reaction buffer before use, added into the experiment holes to reach corresponding final concentration in a 100 μL reaction system. Meanwhile, positive control holes were created, and compound Sorafenib was added. The rest of the stock solutions was storaged at −20° C. after subpackage.

(5) Adding ATP and the tested tyrosine kinase:

ATP solution (ATP final concentration is 5 μM) diluted with reaction buffer was added, and then tested tyrosine kinase diluted with reaction buffer was added. Total volume of the reaction system was 100 μL. Meanwhile, negative control holes and enzyme-free control holes were created.

(6) The reaction system were placed in a wet box, reacted at 37° C. on a shaking table for 1 hour under a condition that light was prohibited, and after the reaction, the plate was washed with T-PBS for three times.

(7) Antibody PY99 100 μL/hole was added, and reacted at 37° C. on a shaking table for 30 minutes. The plate was washed with T-PBS for three times.

(8) Horseradish peroxidase labeled Sheep anti mouse IgG 100 μL/hole was added, and reacted at 37° C. on a shaking table for 30 minutes. The plate was washed with T-PBS for three times.

(9) OPD coloring solution 100 μL/hole was added, and reacted at room temperature for 1~10 minutes under a condition that light was prohibited.

(10) 2M $H_2SO_4$ 50 μL was added to terminate the reaction, and value A490 was measured by tunable wavelength type micro plate (Molecular Devices SPECTRAMAX190).

(11) The inhibition rate of the sample was obtained by the following equation:

Inhibition Rate of Sample % =

$$\left(1 - \frac{OD \text{ value of compound} - OD \text{ value of enzyme} - \text{free control hole}}{OD \text{ value of negative control hole} - OD \text{ value of enzyme} - \text{free control hole}}\right) \times 100\%$$

2. Experimental Results

The inhibition results of typical instantiation compound (III)~compound (VIII) on the activity of DKR receptor tyrosine kinase and PDGFR-β receptor tyrosine kinase are shown in the following Table 1 and Table 2, respectively.

TABLE 1

Inhibition of compounds on activity of VEGFR2 tyrosine kinase

| Compound | Average of $IC_{50}$ (nM) | SD Value |
| --- | --- | --- |
| Compound (III) | 5.1 | 2.5 |
| Compound (IV) | 4.3 | 1.7 |
| Compound (V) | 30.4 | 14.3 |
| Compound (VI) | 47.8 | 3.7 |
| Compound (VII) | 48.3 | 0.3 |
| Compound (VIII) | 21.0 | 10.2 |
| Sorafenib (positive control) | 11.1 | 4.6 |

TABLE 2

Inhibition of a compounds on activity of PDGFR-β tyrosine kinase

| Compound | Average of $IC_{50}$ (nM) | SD Value |
| --- | --- | --- |
| Compound (III) | 25.4 | 13.1 |
| Compound (IV) | 6.7 | 1.6 |
| Compound (V) | 16.3 | 7.0 |
| Compound (VI) | 45.4 | 3.2 |
| Compound (VII) | 105.9 | 21.1 |
| Compound (VIII) | 154.8 | 57.1 |
| Sorafenib (positive control) | 18.4 | 8.6 |

The above pharmacological experiments were implemented by Shanghai Institute of Materia Medica, Chinese Academy of Sciences. $IC_{50}$+SD value and inhibition rate were the average values of 3~4 experiments carried out in different times, respectively, wherein, each tested sample was tested for at least 2 times in each experiment.

The above experimental results confirmed that:

1. The naphthalurea derivatives of the present invention can significantly inhibit phosphorylation of VEGFR2 and PDGFR-β receptor tyrosine kinases at the molecular level, and be new inhibitors of tyrosine kinase.

2. In the listed compounds, inhibition $IC_{50}$ of compound (IV) which had the highest activity on activity of VEGFR2 tyrosine kinases was 4.3 nM, which was 2.6 times of that of positive control Sorafenib ($IC_{50}=11.1$ nM). Inhibition $IC_{50}$ of compound (IV) on activity of PDGFR-β tyrosine kinase was 6.7 nM, which was 2.7 times of that of positive control group Sorafenib ($IC_{50}=18.4$ nM). Control drug Sorafenib has the strongest action in the same kind of medicine in current market. It had shown that compounds with greater biological activity can be found in this series of compounds.

3. Inhibition $IC_{50}$ of compound (V) on activity of PDGFR-β tyrosine kinase was 16.3 nM, which was slightly greater than positive control group Sorafenib ($IC_{50}=18.4$ nM). This compound has a nitrogen atom on with strong alkaline at the side chain. In water-solubility test (22° C., ultrasonic mixing for 24 hours, pH5.5, average of two experiments), the solubility of compound (V) was obviously better than this of compound (III) and compound (IV) without an alkaline side chain. The water solubility of compound (V) was greatly better compound (III), and was 6.9 times of that of compound (IV) as shown in Table 3 which indicates that derivatives with side chains of stronger alkaline had the advantage of better water solubility.

TABLE 3

| | Compound | | |
|---|---|---|---|
| | Compound (III) | Compound (IV) | Compound (V) |
| Solubility in Water | Not Detected | $9.25 \times 10^{-5}$ mg/mL | $6.4 \times 10^{-4}$ mg/mL |

The above experiments showed that: the kind of 1 naphthalurea compounds of the present invention can selectively target specific protein, receptor tyrosine kinase, and is a new kind of multi-target tyrosine kinase inhibitor, can be used in medicines treating diseases or symptoms mediated by tyrosine kinase. These compounds can achieve the effect of inhibiting growth, proliferation and metastasis of tumor cells by acting on VEGFR2 and PDGFR receptors and selectively and effectively inhibiting phosphorylation of receptor tyrosine kinase to block signal transduction in abnormal cells. Meanwhile, these compounds can lead to death of tumor cells by blocking formation of tumor neovascularization, blocking supplies of blood and nutrients required in tumor growth. Besides, the expression of VEGFR2 and PDGFR receptors are mainly limited to proliferative vascular endothelial cells and vascular wall cells, and therefore, with respect to cytotoxic medicines, targeting vascular endothelial growth factor receptor and platelet derived growth factor receptor for treating tumors can have advantages such as high selectivity, high specificity, and low toxicity, etc. In addition, the naphthaurea compounds (compound (II)) of the present invention can be used in medicine for treating age-related macular degeneration or diabetic retinopathy accompanied by pathological neovascularization, and can prevent visual loss caused by choroidal or retinal bleeding and scarring induced by pathological neovascularization by inhibiting phosphorylation of VEGFR2 receptor tyrosine kinase in endothelial cell membranes of pathological neovascularization and in the lesions and phosphorylation of PDGFR-β receptor tyrosine kinase inperithelial cell membranes of vascular wall.

According to the present invention, diseases mediated by tyrosine kinase include malignancies and eye diseases accompanied by pathologic neovascularization. Malignancies include, but not limited to, kidney cancer, liver cancer, colon cancer, gastrointestinal stromal tumor, lung cancer, breast cancer, pancreatic cancer, neural glial tumor, lymph cancer, fibrosarcoma, ovarian cancer, leukemia and prostate cancer, etc. Eye diseases include age-related macular degeneration, diabetic retinopathy and the like.

The embodiments described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

What is claimed is:

1. A naphthalurea derivative being a compound of formula I, and a pharmaceutically acceptable salt, a hydrate, a prodrug thereof,

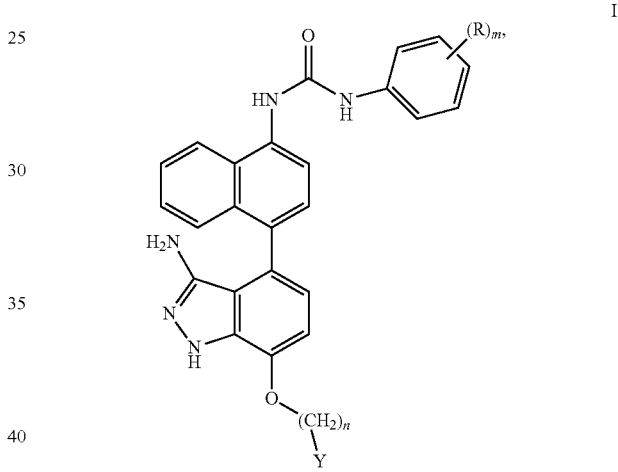

wherein R is selected from the group consisting of: halogen; hydroxyl; sulfhydryl; cyano; amino or alkyl-substituted amino; nitryl; $C_1$-$C_6$ alkyl unsubstituted or substituted by one or more of halogen, hydroxyl, sulfhydryl, cyano, amino, alkyl-substituted amino and nitryl; $C_1$-$C_6$ alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; and $OCOR_9$; wherein, $R_5$, $R_6$, $R_7$, $R_8$, $R_9$, $R_{10}$, and $R_{11}$ are independently selected from $C_1$-$C_6$ alkyl unsubstituted or substituted by halogen;
wherein m is an integer between 0 and 5;
wherein n is an integer between 1 and 5; and
wherein Y is selected from the group consisting of: halogen; hydroxyl; amino or alkyl-substituted amino; $C_1$-$C_3$ alkoxy unsubstituted or substituted by one or more of halogen, hydroxyl, sulfhydryl, cyano, amino and alkyl-substituted amino; and five-membered or six-membered heterocycle containing N and/or O; $CHR_{10}R_{11}NH_2$.

2. The naphthalurea derivative according to claim 1, wherein R is selected from the group consisting of: fluoro, chloro, bromo, iodo, hydroxyl, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, C(=O)CH$_3$, C(=O)CH$_2$CH$_3$, C(=O)NHCH$_3$, C(=O)NHCH$_2$CH$_3$, NHC(=O)OCH$_3$, NHC(=O)OCH$_2$CH$_3$, NHCH$_3$, N(CH$_3$)$_2$, and NHCH$_2$CH$_3$.

3. The naphthalurea derivative according to claim 1, wherein m is 1 or 2.

4. The naphthalurea derivative according to claim 1, wherein n is 2 or 3.

5. The naphthalurea derivative according to claim 1, wherein Y is selected from the group consisting of:

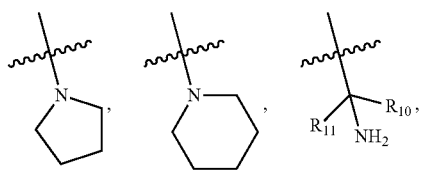

wherein, R$_{10}$ and R$_{11}$ are independently selected from the group consisting of: methyl, halogen-substituted methyl, halogen-substituted ethyl, and propyl or halogen substituted propyl.

6. A naphthalurea derivative being a compound of formula II, and a pharmaceutically acceptable salt, a hydrate, a prodrug thereof,

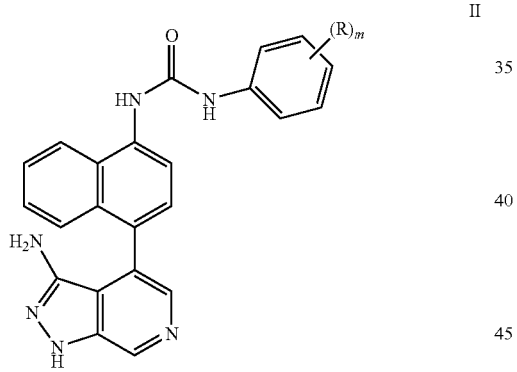

II wherein R is selected from the group consisting of: halogen; hydroxyl; sulfhydryl; cyano; amino or alkyl-substituted amino; nitryl; C$_1$-C$_6$ alkyl unsubstituted or substituted by one or more of halogen, hydroxyl, sulfhydryl, cyano, amino, alkyl-substituted amino and nitryl; C$_1$-C$_6$ alkoxy unsubstituted or substituted by one or more of halogen, hydroxyl, sulfhydryl, cyano, amino, alkyl-substituted amino and nitryl; COR$_5$; CONHR$_6$; COOR$_7$; NHCOR$_8$; and OCOR$_9$, wherein R$_5$, R$_6$, R$_7$, R$_8$ and R$_9$ are independently selected from C$_1$-C$_6$ alkyl unsubstituted or substituted by halogen; and wherein m is an integer between 0 to 5.

7. The naphthalurea derivative according to claim 6, wherein m is 1 or 2, and wherein R is selected from C$_1$-C$_6$ alkyl and halogen.

8. A naphthalurea derivative selected from the group consisting of the following compounds, and a pharmaceutically acceptable salt, a hydrate, a prodrug thereof

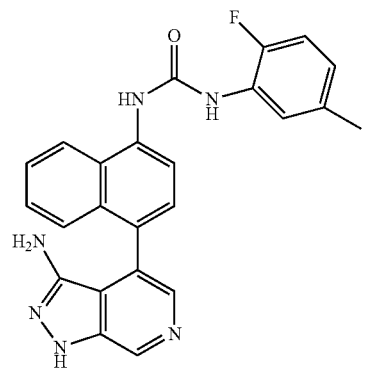

(III)

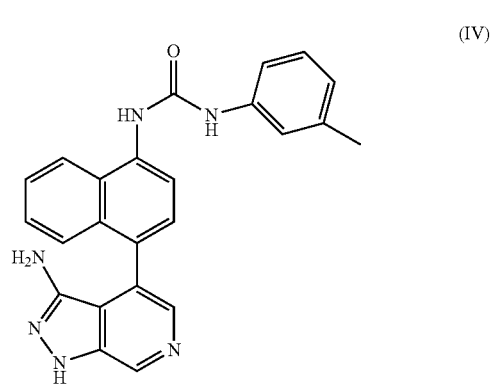

(IV)

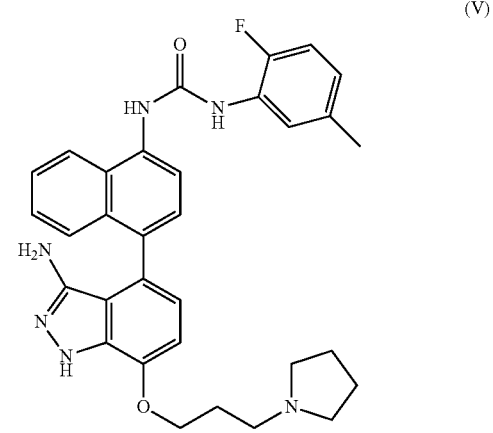

(V)

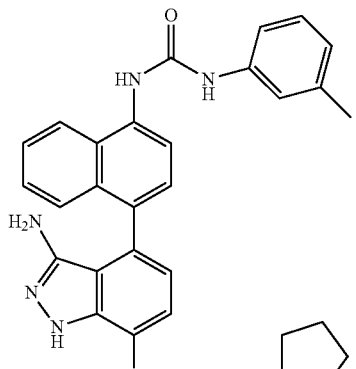

(VI)

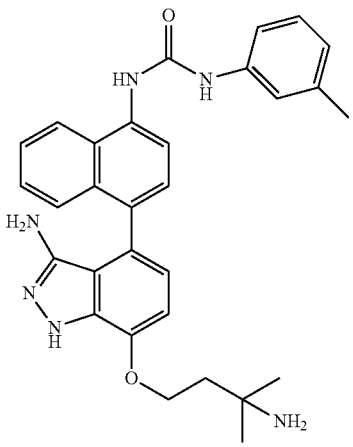

(VIII)

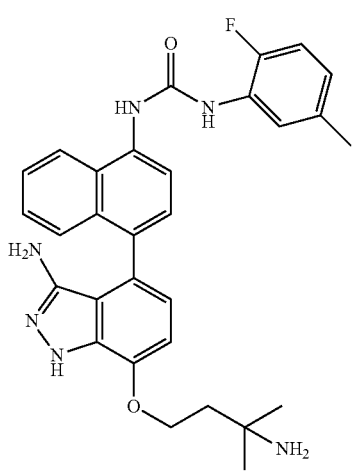

(VII)

9. A pharmaceutical composition for treating tyrosine kinase-mediated diseases or symptoms, comprising an effective amount of the naphthalurea derivative compound of claim 1.

10. A pharmaceutical composition for treating tyrosine kinase-mediated diseases or symptoms, comprising an effective amount of the naphthalurea derivative compound of claim 6.

11. A pharmaceutical composition for treating tyrosine kinase-mediated diseases or symptoms, comprising an effective amount of the naphthalurea derivative compound of claim 8.

12. A method of treating tyrosine kinase-mediated diseases or symptoms in a subject, comprising administering an effective amount of the naphthalurea derivative compound of claim 1.

13. A method of treating tyrosine kinase-mediated diseases or symptoms in a subject, comprising administering an effective amount of the naphthalurea derivative compound of claim 6.

14. A method of treating tyrosine kinase-mediated diseases or symptoms in a subject, comprising administering an effective amount of the naphthalurea derivative compound of claim 8.

* * * * *